US012121382B2

(12) United States Patent
Wang et al.

(10) Patent No.: US 12,121,382 B2
(45) Date of Patent: Oct. 22, 2024

(54) X-RAY TOMOSYNTHESIS SYSTEM PROVIDING NEURAL-NET GUIDED RESOLUTION ENHANCEMENT AND THINNER SLICE GENERATION

(71) Applicant: GE Precision Healthcare LLC, Wauwatosa, WI (US)

(72) Inventors: Dejun Wang, Beijing (CN); Buer Qi, Beijing (CN); Tao Tan, Nuenen (NL); Gireesha Chinthamani Rao, Pewaukee, WI (US); Gopal B. Avinash, Concord, CA (US); Qingming Peng, Beijing (CN); Yaan Ge, Beijing (CN); Sylvain Bernard, Montigny le Bretonneux (FR); Vincent Bismuth, Paris (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 250 days.

(21) Appl. No.: 17/690,258

(22) Filed: Mar. 9, 2022

(65) Prior Publication Data

US 2023/0284986 A1 Sep. 14, 2023

(51) Int. Cl.
*A61B 6/40* (2024.01)
*A61B 6/00* (2006.01)
*A61B 6/02* (2006.01)
*G06N 3/045* (2023.01)
*G06T 3/4046* (2024.01)
*G06V 10/25* (2022.01)

(52) U.S. Cl.
CPC ............ *A61B 6/4429* (2013.01); *A61B 6/025* (2013.01); *A61B 6/5205* (2013.01); *G06N 3/045* (2023.01); *G06T 3/4046* (2013.01); *G06V 10/25* (2022.01)

(58) Field of Classification Search
CPC ....... A61B 6/4429; G06V 10/25; G06N 3/045
See application file for complete search history.

(56) References Cited

U.S. PATENT DOCUMENTS

| 2018/0075581 | A1 | 3/2018 | Shi et al. | |
|---|---|---|---|---|
| 2018/0329609 | A1* | 11/2018 | De Swarte | G06T 19/00 |
| 2019/0325621 | A1* | 10/2019 | Wang | G06N 3/045 |
| 2022/0036608 | A1* | 2/2022 | Wicklein | A61B 6/502 |
| 2022/0318998 | A1* | 10/2022 | Fukuda | G06T 7/0012 |
| 2023/0076352 | A1* | 3/2023 | Zhang | A61B 6/5258 |
| 2023/0125320 | A1* | 4/2023 | Yan | A61B 6/502 |
| | | | | 378/62 |
| 2023/0154006 | A1* | 5/2023 | Gao | G06T 7/0012 |
| | | | | 382/128 |

FOREIGN PATENT DOCUMENTS

| CN | 107358575 A | 11/2017 |
|---|---|---|
| CN | 107464216 A | 12/2017 |
| JP | 2012231901 A | 11/2012 |

OTHER PUBLICATIONS

JP application 2023-006291 filed Jan. 19, 2023—Office Action issued Mar. 13, 2024; Machine Translation; 6 pages.
JP2012231901 English Abstract; Espacenet search Jun. 13, 2024; 1 page.

* cited by examiner

*Primary Examiner* — Hugh Maupin
(74) *Attorney, Agent, or Firm* — Boyle Fredrickson S.C.

(57) ABSTRACT

A tomosynthesis machine allows for faster image acquisition and improved signal-to-noise by acquiring a projection attenuation data and using machine learning to identify a subset of the projection attenuation data for the production of thinner slices and/or higher resolution slices using machine learning.

18 Claims, 3 Drawing Sheets

X-RAY TOMOSYNTHESIS SYSTEM PROVIDING NEURAL-NET GUIDED RESOLUTION ENHANCEMENT AND THINNER SLICE GENERATION

FIELD OF THE DISCLOSURE

The present disclosure relates generally to x-ray tomosynthesis machines, and more particularly to systems and methods for decreasing the acquisition and reconstruction time for high-resolution tomosynthesis images.

BACKGROUND OF THE DISCLOSURE

In tomosynthesis imaging, x-rays, for example, in a cone or parallel beam, is directed through a patient at a range of angles about the patient to be received by a multielement detector. At each angle, the detector collects "projection attenuation data" representing the attenuation of x-ray photons at different angles within the x-ray beam through a volume in the patient and generally having the appearance of a standard x-ray fluoroscopy image. A tomosynthesis reconstruction of a set of projections at different angles about the patient generates attenuation data for a set of voxels of tissue within that volume that can be used to reconstruct images exclusive to a slice in a given plane extending along the superior-inferior axis of the patient.

Tomosynthesis should be distinguished from conventional CT tomography because it works with machines that can move the x-ray source (or x-ray detector) in an arc about the patient having only a limited angular range and thus can be performed on a variety of architectures that may not have the ability to move the x-ray tube fully (360°) about the patient. Similar computed tomography ("CT") machines requires a larger angular range (180° plus the fan beam angle) and normally employs a rotating gantry that circles about the patient. Both tomosynthesis and CT use similar reconstruction algorithms executed by electronic computer and will collectively be referred to as tomography or tomosynthesis machines as used herein and the methods of the present invention can be employed on a CT tomographic system if desired.

The quality of the acquired projection attenuation data from tomosynthesis is a function of the number of samples collected in each projection. This number of samples is largely determined by the size and spacing of the detector elements with smaller sizes and thus closer spacings providing generally higher resolution.

Higher resolution detectors are desirable for increasing the resolution of the image; however, increasing the detector resolution can also greatly increase the time required for data acquisition (with a given signal to noise ratio) increasing patient dose and the risk of blurring from patient motion. High-resolution detectors also collect correspondingly large amounts of data requiring increased time to reconstruct images and potentially imposing additional burdens on the clinician who may be presented with a large number of slice views, some of which may offer little additional information value.

For this reason, high-resolution tomosynthesis machines are often operated at a lower resolution by "binning" together the signals from adjacent detector elements, combining their values, to reduce resolution in favor of higher acquisition speeds and reduced data collection and review burdens.

It would be desirable to develop a system and method for operating a tomosynthesis machine that provides high-resolution imaging while reducing the impact of greatly increased data acquisition and data processing times and the generation of unnecessary slice data for clinician review.

SUMMARY OF THE DISCLOSURE

The present inventors have recognized that the fine structure of the human body revealed by high-resolution images can be successfully taught to a neural network to accurately boost low-resolution images into high-resolution images after acquisition. Fast acquisition of low-resolution data over a relatively large region of interest may be first used to refine the volume of interest. This refined volume of interest may be determined automatically by a trained machine learning system. Once the refined volume of interest is identified, the subset of the acquired data comprising that refined volume of interest can then be converted to a high-resolution image and ultimately presented to the clinician, satisfying the multiple goals of increased resolution, reduced acquisition, and processing time, and reduced superfluous data provided to the clinician According to one aspect of an exemplary embodiment of the disclosure, the invention may provide a tomosynthesis apparatus having a support assembly including an x-ray source and a multielement x-ray detector rotatable in opposition about a patient support; and a processor communicating with the support assembly. The processor is configured to: (a) operate the support assembly to obtain projection attenuation data of a first volume of a patient on the patient support; (b) use machine learning to identify in the first volume a region of interest of clinical significance having a second volume less than the first volume; (c) selectively reconstruct the projection attenuation data of the second volume to produce a first set of slices having a first thickness in the region of interest and a second set of slices having a second thickness larger than the first thickness outside of the second volume; (d) use machine learning to increase the resolution of the first set of slice images; and (e) output the first set and second set of slice images.

It is thus a feature of at least one embodiment of the invention to allow rapidly acquired high signal-to-noise ratio projection attenuation data to be used to generate a higher resolution data set of a clinically interesting region of the patient.

Step (b) may use machine learning to identify a mask region in each projection and then reconstructs those mask regions to provide the second volume to reconstruct the first and the second sets of slices in (c).

It is thus a feature of at least one embodiment of the invention to employee machine learning to develop a region of interest from the raw projection data.

Step (d) may increase the resolution of the first slice images as measured in a plane of the image.

It is thus a feature of at least one embodiment of the invention to allow in-plane resolution enhancement by using machine learning instead of conventional interpolation.

The projection attenuation data may be a set of projections obtained with x-ray beams directed across a patient inferior-superior axis at various angles, and the second volume of the patient may have a reduced height compared to the first volume measured perpendicular to the patient axis.

It is thus a feature of at least one embodiment of the invention to provide high resolution thin slices while reducing the number of slices that the clinician needs to review.

In some embodiments, the neural network is trained using an adversarial neural network architecture such as a Wasserstein Generative Adversarial Network (WGAN). The neural network maybe trained using an evaluation of at least one of error difference between generated and training set data and VGG processing of high- and low-resolution images.

It is thus a feature of at least one embodiment of the invention to identify a tractable neural net architecture and training technique for this purpose.

The x-ray detector may have a given detector spacing between independent detector elements, and the low-resolution tomosynthesis attenuation data is obtained by binning together the values from adjacent detector elements.

It is thus a feature of at least one embodiment of the invention to permit faster acquisition and improve signal-to-noise ratio by binning the detectors with reduced loss of resolution.

It should be understood that the brief description above is provided to introduce in simplified form a selection of concepts that are further described in the detailed description and shown in the accompanying drawing figures. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode currently contemplated of practicing the present disclosure.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Figure 1:
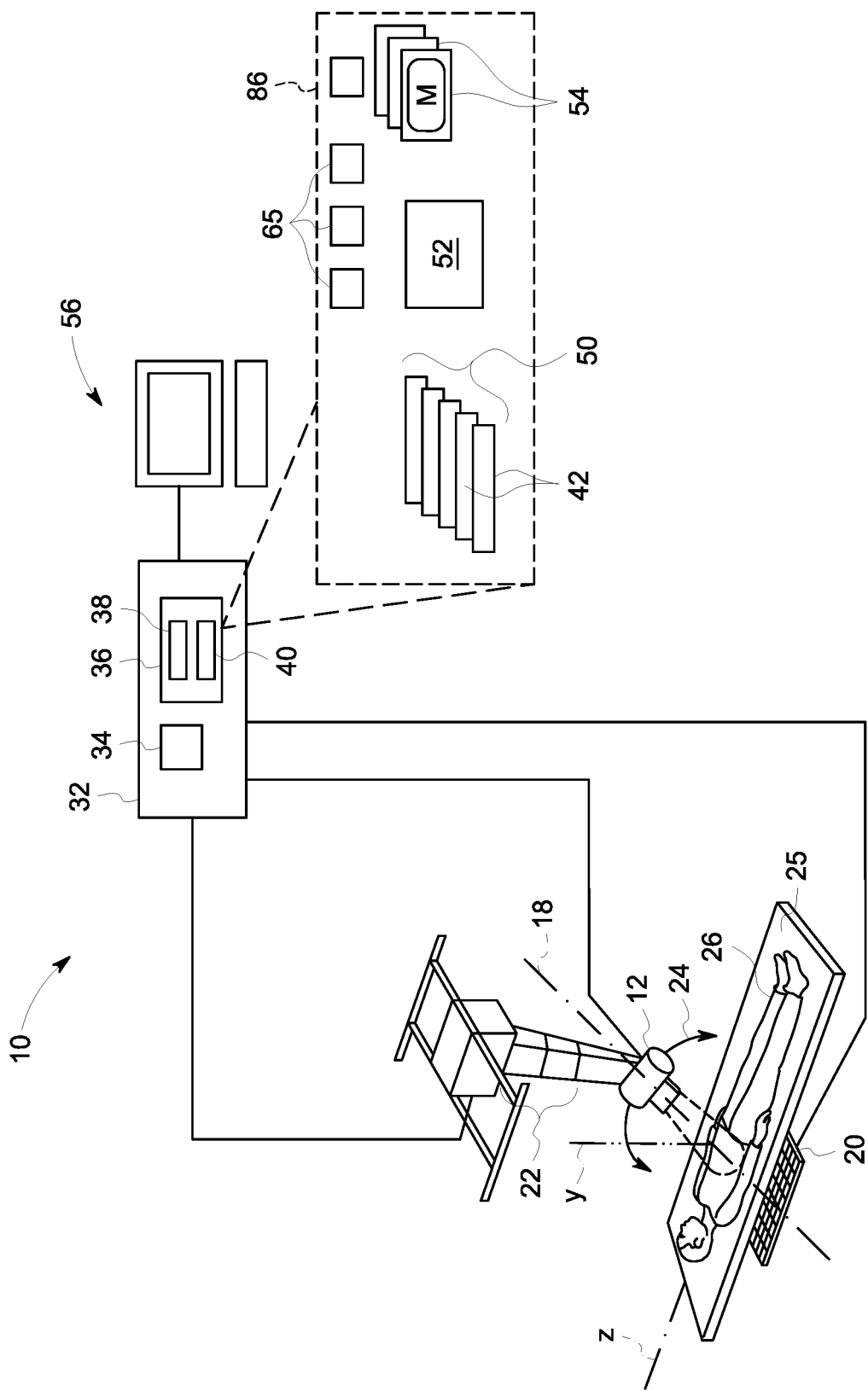
FIG. 1 is a simplified block diagram of an x-ray tomosynthesis machine showing the principal components of an x-ray tube, a multielement x-ray detector, and a processor that can perform tomosynthesis reconstructions.

Referring now to FIG. 1, an X-Ray tomosynthesis machine may provide an x-ray source 12 producing a beam 16 of x-rays directed along a projection axis 18 toward a detector 20. The x-ray source 12 may be mounted on an articulating arm assembly 22 that may be rotated by a motor/encoder system along an arc 24 so that the angle of the axis 18 may intersect a detector 20 at a range of angles.

A radiolucent patient table 25 may extend generally along a z-axis to support a patient 26 whose inferior-superior axis is parallel to the z-axis. The patient table 24 is positioned between the x-ray source 12 and the detector 20 to support the patient 26 so that the x-rays of the beam 16 pass through the patient 26 during rotation of the articulating arm assembly 22. After passing through the patient volume 28, the x-rays are measured by the detector 20 over a variety of detector elements 21 each individually measuring x-ray attenuation. Generally, the angle of the arc 24 will be less than 180° allowing the system to be readily integrated into a standard x-ray system including digital radiography, mammography and fluoroscopy, however it will be appreciated that the invention is equally applicable to a CT type design having greater rotational freedom.

Each of the x-ray source 12, motor/encoder system of the articulating arm assembly 22, and detector 20 may communicate with a tomosynthesis controller 32 providing one or more processors 34 communicating with an electronic memory 36 that may hold a stored program 38 and data 40. Generally, the program 38 may execute to provide for rotation of the articulating arm assembly 22 through a range of angles of the axis 18 and, at each angle, acquisition of a projection 42 made up of the independent x-ray attenuation measures of each of the detector elements 21. A projection set 50, including measurements at a range of angles and may be stored as data 40. The resulting projections set describes a region or volume of interest in the patient volume 26.

As is generally understood in the art, the program 38 may further implement a tomosynthesis reconstructor 52 that takes each projection set 50 and reconstructs it into slices representing the attenuation in a set of stacked planes within the patient, the data of the slices together describing attenuation of multiple individual volume elements (voxels) in a volume of the patient 26. Each of the slices provides a cross-sectional images 54, for example, in a set of image planes stacked vertically (along a y-axis) through the patient 26 above the patient table 25. As used herein, both the projections 42 and the images 54 will generally be referred to as tomosynthesis attenuation data, reflecting their mathematical equivalence.

Referring still to FIG. 1, the controller 32 may communicate with a user interface 56, for example, a graphic display terminal, keyboard, mouse, or the like, to allow data 40 to be output to a clinician or technician and data 40 to be received therefrom for the execution of the program 38 as discussed further below.

Figure 2:
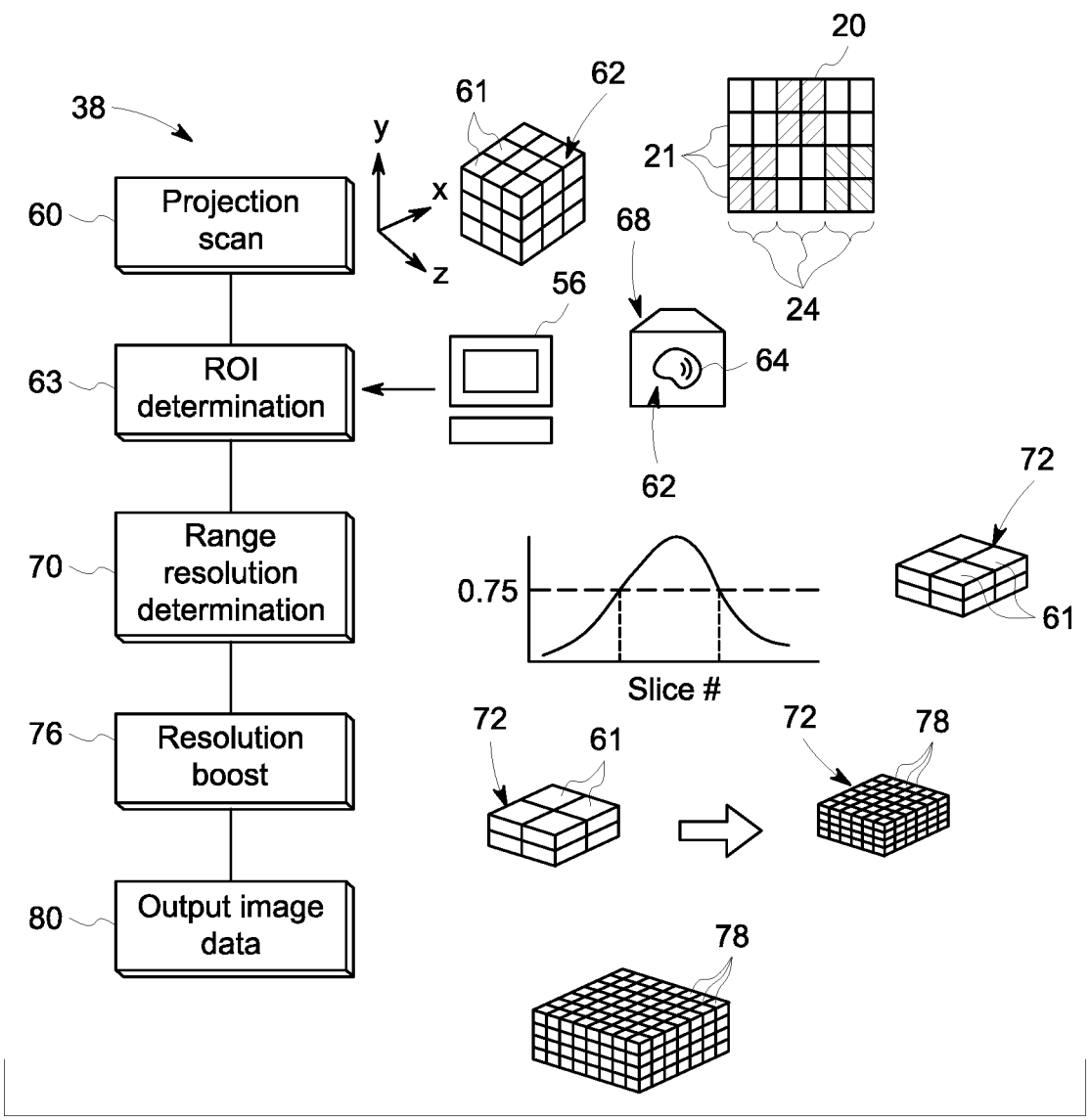
FIG. 2 is a flowchart showing operation of the tomosynthesis machine to FIG. 1 under the control of a program executed by the processor.

Referring now also to FIG. 2, the program 38, as indicated by process block 60, may control the various components of the tomosynthesis machine 10 as discussed above to make a 1 scan of the patient volume 26 resulting the acquisition of reduced resolution tomosynthesis attenuation data 61 over acquisition volume 62 being represented either as projection sets or images as desired over a first volume of the patient 26.

This low-resolution scan may use a detector 20, with inherently low resolution or more typically may use a high-resolution detector 20 by binning or combining the values of clusters of detector elements 21, for example, by averaging together the values of four adjacent detector elements 21. For example, if the separation between the detector elements 21 is 100 µm, the binning may produce an effective separation between attenuation measurements of 200 µm. The binning process may be performed during scanning or after data has been collected and thus may combine detector elements 21 within a single slice 28 or between slices 28. This binning process provides the advantages of higher-speed scanning and/or reduced x-ray dose for a given signal to noise ratio signal.

As indicated by process block 63, a desired region of clinical focus, for example, a disease region, may then be determined, typically being less than the volume of the patient 26 for which tomosynthesis data has been acquired. For example, this region can be a subset or smaller focus portion 64 of an acquisition volume 62 representing an entirety of the acquired tomosynthesis attenuation data. In one embodiment, the clinician may enter clinical indication such as a disease, and the data of the acquisition volume 62 may be automatically segmented by a neural network 65 trained to identified disease tissue associated with that entered disease. In this respect the program 38 may implement a set of trained neural networks 65 each associated with the different clinical condition or disease. These neural networks 65 may each be trained using a training set comprised of different tomosynthesis data associated with a particular disease where disease manifestations, for example, tumors, have been segmented for example by human experts. The neural network 65 reviewing the data of the acquisition volume 62 may then produce a volume mask 68, for example, defining as focus portion 64, tumors in a particular organ.

Alternatively, the data of the acquisition volume 62 may be provided simultaneously to multiple neural networks 65 each trained on a different disease or clinical condition to broadly define the region of interest as relating to any disease within the training experience of any of the neural network 65.

In one embodiment, the neural network(s) 65 may work directly on the projection attenuation data before reconstruction to identify mask regions within each slice of the pre-reconstructed data. These masks may then be reconstructed to provide the focus portion 64.

At process block 70, program 38 uses the volume mask 68 to "curate" the tomosynthesis attenuation data 61 of the acquisition volume 62 by separate processing of the reduced resolution tomosynthesis attenuation data 61 outside of a smaller volume 72, the smaller volume 72 containing only tomosynthesis data clinically relevant to the focus portion 64. The smaller volume 72 may, for example, have a reduced height along the z-axis compared to the acquisition volume 62 to match the height of the volume mask 68. This will reduce the number of thin in-plane images necessary to accurately describe the region of the volume masks 68. A more sophisticated approach evaluates each data plane (data elements of constant value y) of the acquisition volume 62 with respect to the information related to a disease being investigated to consider the information value of that data plane. Only data planes having an information value of above a predefined threshold (for example, 0.75 normalized to one) are then included in the smaller volume 72. This evaluation of information contribution may be performed, for example, by analyzing the likelihood that delivered by deep learning network for the disease to determine interest of slice range for each tomosynthesis series, the slices with higher likelihood indicate that this slice shows the information for the disease. At the conclusion of process block 70, two sets of slices will be produced with slices in the smaller volume 72 being thinner than slices outside of the smaller volume 72.

At succeeding process block 76, the reduced-resolution data 61 of the smaller volume 72 may then be boosted to provide super-resolution data 78 for that same smaller volume 72, the higher, super-resolution data 78 approximating that obtained with closer spacings of the detector elements 21 both along the detector 20 and along the z-axis. A variety of boosting techniques may be used including, for example, interpolation; however, in one embodiment this boosting makes use of a trained neural network 86 to be described below. The trained neural network 86 may have a set of weights related generally to all human anatomy or may provide different sets of weights for different tissue types, for example, bone, organ tissue, muscle tissue, and the like, which may be selected by the clinician depending on the application and the tissue in the volume mask 68. Likewise this tissue may be automatically catalogued and used to define a set of weights.

Thus, for example, an acquisition volume 62 beginning at a height of 20 mm above the table 25 and proceeding to a height of 280 mm above the table 25 and having an image plane height of 10 mm may provide for 27 images. The resulting slice thickness may be preserved for regions of the patient outside of the smaller volume 72. The smaller volume 72, on the other hand, may start at 100 mm and proceed to a height of 170 mm with an image height of 4 mm for a total number of images of 19, greatly reducing the data necessary for review by the clinician while providing higher resolution through a narrower image height. The ability to boost only the data in the smaller volume 72 allows great flexibility in setting the image plane height, for example, according to preferences set by the clinician. Also this can be determined automatically by deep learning network for the disease diagnosis. Specifically, we obtain the likelihood of disease like pneumonia for each slices and extracted the slice height with higher likelihood of pneumonia.

At process block 80, the boosted super-resolution data 78 may be output, for example, to the user interface 56 in the form of a set of stacked slice images 54 that may be viewed by the clinician. The un-boosted data from outside of the smaller volume 72 is also provided for context to provide collected images of a single volume for example equal to the acquisition volume 62. It will be appreciated that the benefits of high resolution closely linked to the region of interest of smaller volume 72 are obtained without the need to process and collect high-resolution data with respect to the acquisition volume 62. Further, the ability to initially collect reduced-resolution data allows extra data to be collected to permit localization of the smaller volume 72 without the acquisition time penalty required if high-resolution data were necessary for the entire acquisition volume 62. Taking postero-anterior X-Ray tomosynthesis slices as an example, some slices will have particular clinical significance as revealing fracture information, and the present invention may use thinner slices with boosted resolution to increase the resolution for the slices with fracture.

Figure 3:
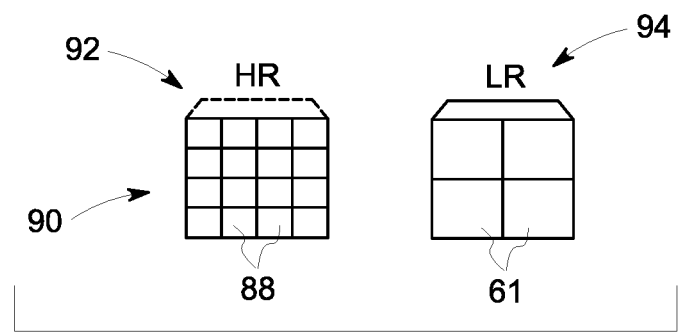
FIG. 3 is a logical diagram showing a projection attenuation data acquired by the tomosynthesis machine of FIG. 1 and a down-sampled, lower-resolution image used to construct a training set.
Figure 4:
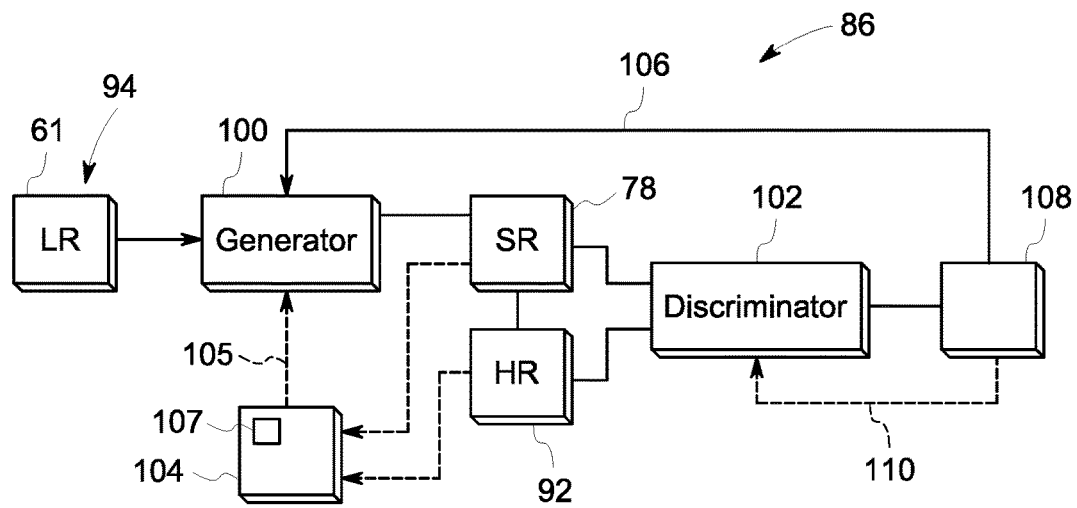
FIG. 4 is a block diagram of an adversarial neural network system used for boosting data showing its training and operation flow paths.

Referring now to FIGS. 3 and 4, the present inventors have determined that high-quality boosting of reduced-resolution data 61 can be effectively performed by a programmed neural network 86 operating to receive reduced-resolution data 61 (LR) and to produce corresponding super-resolution data 78 (SR) generally of comparable resolution to natively acquired high-resolution data 88. In order to train this neural network 86, a training set 90 is generated for each class of tissue on which boosting will be performed or for a general class embracing all tissue types. The training set consists 90 of a high-resolution data set 92 taken on a high-resolution tomosynthesis machine 10 without binning of the detector elements 21. So, for example, on a detector 20 having an inter-detector spacing of 100 μm, the high-resolution data 88 of the data set 92 will be such as to provide a voxel separation of roughly 100 μm (influenced by the geometry of the fan beam 16). This high-resolution data 88 of the data set 92 may be then converted to a reduced-resolution data set 94 having reduced-resolution data 61 covering the same volume by the binning process described above. A training set 90 consists of multiple linked pairs of high-resolution data sets 92 and reduced-resolution data sets 94. It will be appreciated that the training set 90 can make use of any of direct projection data or tomosynthesis reconstructed volume or image plane data.

In order to reduce the amount of data that is necessary to be boosted by the neural network 86, the high-resolution data 88 of the high-resolution data set 92 and the reduced-resolution data 61 of the reduced-resolution data set 94 may be broken into equal area patches (not shown), typically covering equal patient volumes. To eliminate discontinuities at the edges of the patches, the patches may overlap slightly with each other. So, for example, if the high-resolution data set 92 is divided into N×N patches, the patches may be strided at 4N/5 to overlap with neighbor patches. Corresponding patches in reduced-resolution data set 94 will have a stride of 8N/5 as a result of differences in sampling.

Referring to FIG. 4, in one embodiment, programmed neural network 86 may have an adversarial neural network architecture and, in one example, be a Wasserstein Generative Adversarial Network (WGAN). This type of architecture includes a first neural network providing a generator 100 for generating super-resolution data 78 from reduced-resolution data 61 (for example, on a patch by patch basis) per process block 76 described above. The generator 100 is trained using a second neural network (discriminator 102) operating to evaluate the super-resolution data 78 and a loss calculator 104.

Generally, the training will proceed in epochs consisting of the training of the generator 100 while the discriminator 102 guide the generator during the training of generator, followed by training of the discriminator 102 while the generator is frozen. Multiple epochs of training are conducted. The generator 100 and discriminator 102 are used adversarially to improve the training of the generator 100 during training. Ultimately, generator 100 is used alone for the purpose of process block 76.

During training of the generator 100, successive reduced-resolution data sets 94 of the training set 90 are presented to the generator 100 to generate a super-resolution data 78. The resulting super-resolution data 78 and the corresponding high-resolution data set 92 are then provided to a loss calculator 104 which provides a loss measure 105 relating to how perceptively similar the super-resolution data 78 is to the high-resolution data set 92. In one embodiment, the loss measure 105 may be a weighted combination of mean square error (MSE) on the spatial domain of the super-resolution data 78 and high-resolution data set 92 and on the Fourier domain (frequency domain) of those same images. The MSE measures may be combined with a measure of VGG loss obtained from a VGG neural network 107 incorporated into the loss calculator 104 also operating on both the super-resolution data 78 and high-resolution data set 92 and providing a measure of VGG loss by comparing the layer feature maps of the VGG neural network with for these two inputs. The VGG neural net 107 may be trained to classify types of tissue. An example of such a loss measure is described in K. Simonyan and A. Zisserman, "Very deep convolutional networks for large-scale image recognition," in International Conference on Learning Representations (ICLR), 2015. This loss measure 105 is provided back to the generator 100 as part of the training process. VGG loss is part of content loss for generator network.

Super-resolution data 78 generated by the generator 100 may also be used to train the discriminator 102 to determine a likelihood that the super-resolution data 78 is a natively obtained HR image represented by high-resolution data set 92 (being a measure of their similarity). The discriminator 102 compares successive sets of super-resolution data 78 generated by reduced-resolution data sets 94 with the corresponding data of the high-resolution data set 92 of the training set 90 which is standard classification network. 102.

After the generator 100 and discriminator 102 have been trained, they are operated together for further training of the generator 100 through an objective function provided by the discriminator 102. Upon completion of the training, the neural weights of the generator 100 are saved to be used for process block 76 of the program 38 described above with respect to a particular tissue type.

The generator 100 and discriminator 102 may be constructed generally according to the designs described in Photo-Realistic Single Image Super-Resolution Using a Generative Adversarial Network, Christian Ledig, Lucas Theis, Ferenc Huszar, Jose Caballero, Andrew Cunningham, Alejandro Acosta, Andrew Aitken, Alykhan Tejani, Johannes Totz, Zehan Wang, Wenzhe Shi, arXiv.org>cs>arXiv:1609.04802.

Figure 5:
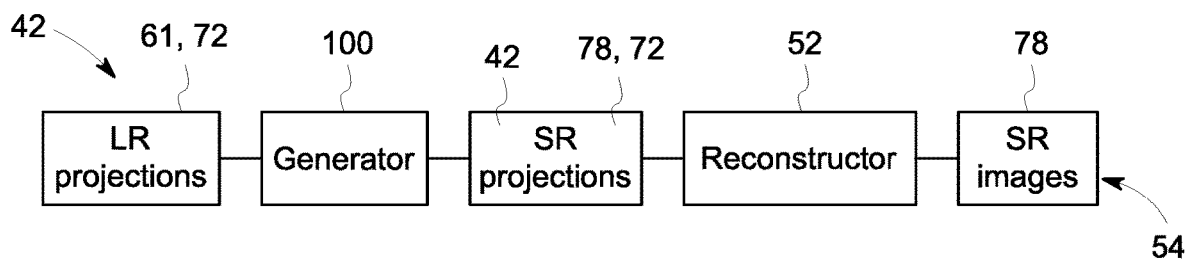
FIG. 5 is a flowchart of an embodiment of the invention providing resolution boosting of projection attenuation data.

Referring now to FIG. 5, it will be appreciated that the boosting may be done directly on the acquired projections 42 obtained during the scan of process block 60 (shown in FIG. 2) operating as the reduced-resolution data 61, and this data can be received by the generator 100 to produce the super-resolution data 78 in the form of super-resolution projections 42. These latter projections 42 may be provided to a tomosynthesis reconstructor 52 (for example, employing filtered back projection) to provide resultant slice images 54 having super-resolution data 78.

Figure 6:
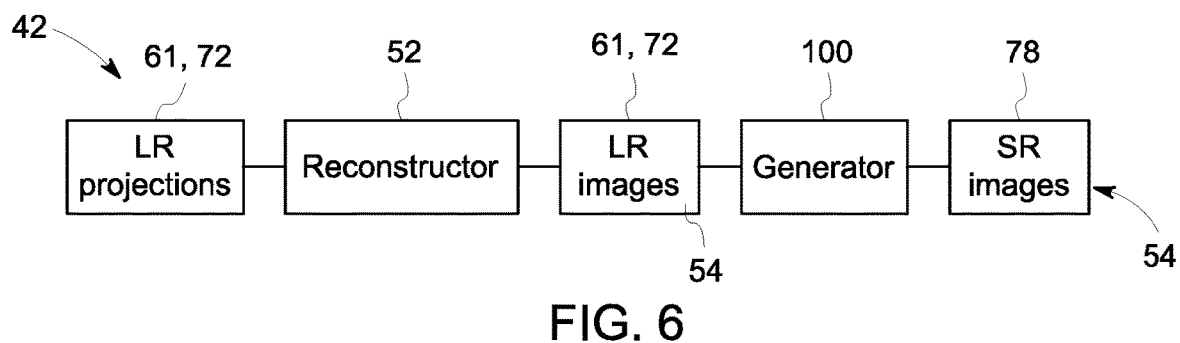
FIG. 6 is a figure similar to that of FIG. 5 showing alternative resolution boosting of reconstructed images.

Alternatively, as shown in FIG. 6, reduced-resolution projections 42 may be provided to the reconstructor 52 to produce reduced-resolution slice images 54 operating as reduced-resolution data 61 which may be provided to the generator 100 to produce high-resolution slice images 54 having super-resolution data 78.

The higher resolution data can be applied to all slices or projections and also can be applied to specific slices or projections that includes significant clinical information or clinician interests. It will be understood that the term "slice thickness" can refer to the separation between centerlines of the slices perpendicular to their planar extent or the thickness of the volume defined by the slice generally perpendicular to the plane of the slice. As used herein, the term "volume" when referring to data represents a set of slice images or the raw data used to reconstruct slice images as will be evident from context.

It is understood that the aforementioned compositions, apparatuses, and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A tomosynthesis apparatus, comprising:
a support assembly including an x-ray source and a multielement x-ray detector rotatable in opposition about a patient support; and
a processor communicating with the support assembly and configured to:
(a) operate the support assembly to obtain reduced-resolution projection attenuation data of a first volume of a patient on the patient support;
(b) use machine learning to identify in the first volume a region of interest of clinical significance having a second volume less than the first volume, the region of interest of clinical significance being a disease region within the first volume;
(c) selectively reconstruct the projection attenuation data of the second volume at a high resolution to produce a first set of slices having a first slice thickness and high resolution in the region of interest and a second set of slices having a second slice thickness larger than the first slice thickness and reduced resolution outside of the second volume; and
(d) output the first set and second set of slice images to provide an image of a single volume including the first volume and the second volume.

2. The tomosynthesis apparatus of claim 1 wherein step (b) uses machine learning to identify a mask region in each projection and then reconstructs those mask regions to provide the second volume to reconstruct the first and the second sets of slices in (c).

3. The tomosynthesis apparatus of claim 1 further including using machine learning to increase the resolution of the first set of slice images as measured in a plane of the image.

4. The tomosynthesis apparatus of claim 1 wherein the projection attenuation data is a set of projections obtained with x-ray beams directed across a patient inferior-superior axis at various angles, and wherein the second volume of the patient has a reduced height range compared to the first volume measured perpendicular to the patient axis.

5. The tomosynthesis apparatus of claim 1 wherein the machine learning is an adversarial neural network architecture.

6. The tomosynthesis device of claim 5 wherein the machine learning is a Wasserstein Generative Adversarial Network (WGAN).

7. The tomosynthesis device of claim 6 wherein the machine learning is trained using an evaluation of at least one of error difference between the generated and training set data and VGG processing of high- and reduced-resolution images.

8. The tomosynthesis device of claim 1 wherein the x-ray detector has a detector spacing between independent detector elements, and the projection attenuation data is obtained by binning together values from adjacent detector elements.

9. A tomosynthesis apparatus, comprising:
a support assembly including an x-ray source and a multielement x-ray detector rotatable in opposition about a patient support; and
a processor communicating with the support assembly and configured to:
(a) operate the support assembly to obtain projection attenuation data of a first volume of a patient on the patient support;
(b) use machine learning to identify in the first volume a region of interest of clinical significance having a second volume less than the first volume;
(c) selectively reconstruct the projection attenuation data of the second volume to produce a first set of slices having a first slice thickness in the region of interest and a second set of slices having a second slice thickness larger than the first slice thickness outside of the second volume; and
(d) output the first set and second set of slice images to provide an image of a single volume,
wherein the x-ray detector has a detector spacing between independent detector elements, and the projection attenuation data is obtained by binning together values from adjacent detector elements, and
wherein the detector elements have a spacing of no more than 100 μm, and the reduced-resolution tomosynthesis data has a resolution of less than twice the spacing.

10. A method of operating a tomosynthesis apparatus the type having a support assembly including an x-ray source and a multielement x-ray detector rotatable in opposition about a patient support comprising:
(a) operating the support assembly to obtain reduced-resolution projection attenuation data of a first volume of a patient on the patient support;
(b) using machine learning to identify in the first volume a region of interest of clinical significance having a second volume less than the first volume, the region of interest of clinical significance being a disease region within the first volume;
(c) selectively reconstructing the projection attenuation data of the second volume at a high resolution to produce a first set of slices having a first slice thickness in the region of interest and a second set of slices having a second slice thickness larger than the first slice thickness outside of the second volume; and
(d) outputting the first set and second set of slice images to provide an image of a single volume including the first volume and the second volume.

11. The method of claim 10 wherein (b) uses machine learning to identify a mask region in each projection and then reconstructs those mask regions to provide the identify the second volume to reconstruct the first and the second sets of slices in (c).

12. The method of claim 10 wherein step (d) increases the resolution of the first slice images as measured in a plane of the image.

13. The method of claim 10 wherein the projection attenuation data is a set of projections obtained with x-ray beams directed across a patient inferior-superior axis at various angles, and wherein the second volume of the patient has a reduced height compared to the first volume measured perpendicular to the patient axis.

14. The method of claim 10 wherein the machine learning is an adversarial neural network architecture.

15. The method of claim 14 wherein the machine learning is a Wasserstein Generative Adversarial Network (WGAN).

16. The tomosynthesis device of claim 10 wherein the machine learning is trained using an evaluation of at least one of error difference between the generated and training set data and VGG processing of high- and reduced-resolution images.

17. The method of claim 10 wherein the x-ray detector has a detector spacing between independent detector elements, and the projection attenuation data is obtained by binning together values from adjacent detector elements.

18. A method of operating a tomosynthesis apparatus the type having a support assembly including an x-ray source and a multielement x-ray detector rotatable in opposition about a patient support comprising:
   (a) operating the support assembly to obtain projection attenuation data of a first volume of a patient on the patient support;
   (b) using machine learning to identify in the first volume a region of interest of clinical significance having a second volume less than the first volume;
   (c) selectively reconstructing the projection attenuation data of the second volume to produce a first set of slices having a first slice thickness in the region of interest and a second set of slices having a second slice thickness larger than the first slice thickness outside of the second volume; and
   (d) outputting the first set and second set of slice images to provide an image of a single volume,
   wherein the x-ray detector has a detector spacing between independent detector elements, and the projection attenuation data is obtained by binning together values from adjacent detector elements, and
   wherein the detector elements have a spacing of no more than 100 μm, and the reduced-resolution tomosynthesis data has a resolution of less than twice the spacing.

* * * * *